US010206392B2

(12) United States Patent
Kloeppel et al.

(10) Patent No.: US 10,206,392 B2
(45) Date of Patent: Feb. 19, 2019

(54) FAST ACTING DISINFECTION COMPOSITION

(71) Applicant: Lonza, Inc., Allendale, NJ (US)

(72) Inventors: Andrew Kloeppel, Harrington Park, NJ (US); James Bargmann, Midland Park, NJ (US)

(73) Assignee: Lonza, Inc., Allendale, NJ (US)

( * ) Notice: Subject to any disclaimer, the term of this patent is extended or adjusted under 35 U.S.C. 154(b) by 282 days.

(21) Appl. No.: 14/681,497

(22) Filed: Apr. 8, 2015

(65) Prior Publication Data
US 2015/0282480 A1 Oct. 8, 2015

Related U.S. Application Data

(60) Provisional application No. 61/976,822, filed on Apr. 8, 2014.

(51) Int. Cl.
*A61L 2/18* (2006.01)
*C11D 1/62* (2006.01)
*A01N 33/12* (2006.01)

(52) U.S. Cl.
CPC .................... *A01N 33/12* (2013.01)

(58) Field of Classification Search
CPC ...................................... A01N 33/12
USPC .......................................... 422/28
See application file for complete search history.

(56) References Cited

U.S. PATENT DOCUMENTS

| 5,529,713 A | 6/1996 | Gauthier-Fournier |
| 2009/0105195 A1* | 4/2009 | O'Brien ................. A01N 25/04 514/56 |
| 2010/0279906 A1* | 11/2010 | Schwarz ............... A23L 3/3463 510/111 |
| 2012/0157540 A1 | 6/2012 | McGeechan et al. |

FOREIGN PATENT DOCUMENTS

| EP | 0099209 A1 | 1/1984 |
| EP | 687727 | * 12/1995 |
| EP | 0827691 A1 | 3/1998 |
| EP | 1277403 A1 | 1/2003 |
| FR | 2622397 A1 | 5/1989 |
| WO | 95/12976 A1 | 5/1995 |
| WO | 2006/116778 A2 | 11/2006 |
| WO | 2009/037445 A1 | 3/2009 |
| WO | 2009/117299 A2 | 9/2009 |
| WO | 2012/080918 A2 | 6/2012 |
| WO | 2013/061082 A1 | 5/2013 |

OTHER PUBLICATIONS

Lonza: "Bardac™ 205M Bardac™ 208M Quaternary Ammonium Compounds EPA Registered", http://lbio.lonza.com/uploads/tx_mwaxmarketingmaterial/Lonza_ProductDataSheets_Bardac_288M_PDS.pdf, Jul. 29, 2007 (Jul. 29, 2007), pp. 1-2, Retrieved from the Internet: URL:http://bio.lonza.com/uploads/tx_mwaxmarketingmaterial/Lonza_ProductDataSheets_Bardac_208M_PDS.pdf, [retrieved on May 22, 2015] Bardac 205M; Bardac 208M.

* cited by examiner

Primary Examiner — Sean E Conley
Assistant Examiner — Holly M Mull
(74) Attorney, Agent, or Firm — Lucas & Mercanti, LLP

(57) ABSTRACT

The present invention relates to a disinfecting composition which requires a shorter contact time to be effective than similar compositions. Also, provided is a method of disinfecting a surface with the disinfecting composition where a shorter contact time is needed to disinfect the surface.

12 Claims, No Drawings

FAST ACTING DISINFECTION COMPOSITION

CROSS-REFERENCE TO RELATED APPLICATION

This application claims priority under 35 U.S.C. § 119(e) from Provisional Application No. 61/976,822 filed Apr. 8, 2014, the disclosure of which is incorporated herein by reference.

FIELD OF THE INVENTION

The present invention relates to a disinfecting composition which requires a shorter contact time to be effective than similar compositions. Also, provided is a method of disinfecting a surface with the disinfecting composition where a shorter contact time is needed to disinfect the surface.

BACKGROUND OF THE INVENTION

The current US Environmental Protection Agency guidelines under the Federal Insecticides, Fungicides and Rodenticide Act (FIFRA), all antimicrobial products are required to demonstrate efficacy against organisms listed on a product label. The methodologies for determining efficacy are organism and use specific. One such test is the AOAC Use Dilution Test (UDT) of 2012. In the Use Dilution Test, efficiency against *Pseudomonas aeruginosa* (Pa) (test method 964.02), *Salmonella enterica* (Se) (test method 955.14) and *Staphylococcus aureus* (Sa) (test method 955.15), each test method incorporated herein by reference, are required for products which are sold as hospital level disinfectants. Generally, these products are sold as concentrates and are diluted by the end user prior to use.

To pass the Use Dilution Test for hospital-strength disinfection, the current requirement as of the filing date of this application, requires no more than one positive tube growth out of sixty (60) test tubes. In addition, there must be three distinct and separate batches of the composition tested. Each organism is tested in same manner. Current standards require that the biocidal products must meet a 10 minute contact time. However, new standards are currently being considered for adoption which will probably require contact times less than 10 minutes.

Accordingly, there is a need in the art for quat based disinfecting compositions and dilatable concentrates which will pass a UDT with a contact time of less than 10 minutes. The present invention provides an answer to that need. The inventors have discovered a quat based disinfecting composition that will meet or exceed a 5 minute contact time.

SUMMARY OF THE INVENTION

In one aspect, the present invention provides a disinfectant concentrate which is dilutable to a disinfectant composition having a 5 minute or less contact kill time, as measured by the Use Dilution Test of 2012. The concentrate contains a) a disinfecting component comprising a mixture of (i) a dimethyldialkyl ammonium compound, wherein each of the alkyl groups of the compound contains between 8 and 10 carbon atoms, and (ii) an alkyl dimethyl benzyl ammonium compound, wherein the alkyl group contain between 12 and 18 carbon atoms. The weight ratio of component (i) to component (ii) is between 4:1 to 1:2. Also present in the concentrate composition is a surfactant (referred to herein as component b). The surfactant may be a nonionic surfactant or a cationic surfactant. Another component in the concentrate is a solvent (component c). Optional component include a sequestering agent (component d) and an optional pH adjuster (component e).

In a further embodiment of the present invention, the disinfectant concentrate is diluted with water to form a disinfectant composition which is to be used as a disinfectant.

In another embodiment of the invention, the surfactant is a nonionic surfactant which is an alkoxylated alcohol surfactant having 2-8 moles of alkoxylation. In a further embodiment of the invention, the surfactant is cationic surfactant which is an alkyl trimethyl ammonium salt, where the alkyl group has at least 8, generally between 10 and 18 carbon atoms.

In a further embodiment of the disinfectant concentrate and disinfectant composition, each of the alkyl groups of the dimethyldialkyl ammonium compound contains between 8 and 10 carbon atoms and the alkyl group of the alkyl dimethyl benzyl ammonium compound contains between 12 and 18 carbon atoms.

In an additional embodiment of the present invention, the alkyl groups of the dimethyldialkyl ammonium compound are each octyl groups.

In a further embodiment of the disinfectant concentrate and composition of the present invention, the dimethyldialkyl ammonium compound comprises dimethyldioctyl ammonium chloride.

In yet another embodiment of the disinfectant concentrate and composition of the present invention, the weight ratio of dimethyldialkyl ammonium compound to the alkyl dimethyl benzyl ammonium compound is between 2:1 to 1:1, more particularly about 1.5:1.

In another embodiment of the present invention, provided is method of disinfecting a surface. The method includes applying the disinfectant composition according to any one of the embodiments of the present invention on a surface, leaving the disinfectant composition in contact with the surface for a period of time, and removing the composition from the surface.

These and other aspects will become apparent when reading the detailed description of the invention.

DETAILED DESCRIPTION OF THE EMBODIMENTS

It has now been surprisingly found that a disinfectant concentrate described herein may be diluted with water to form a disinfecting composition that will pass the Use Dilution Test with a less than 10 minute contact time.

As used herein, the term "disinfectant concentrate" means a composition which may be diluted with water prior to use. In the disinfectant concentrate, the amount of the disinfecting component will be higher than typical use amounts.

As used herein, the term "disinfectant composition" or "disinfecting composition" is intended to mean a composition which contains the disinfecting component in an amount that is suitable for use to disinfect a substrate.

The disinfectant concentrate, which is dilutable to a disinfectant composition having a 5 minute or less contact kill time, as measured by the Use Dilution Test, contains a disinfecting component, a surfactant, a solvent and optionally a sequestering agent and a pH adjuster. The disinfecting component is a mixture of quaternary ammonium compound.

Quaternary ammonium compounds, also known as "quats", typically comprise at least one quaternary ammonium cation with an appropriate anion. Quats will generally have the general formula (1).

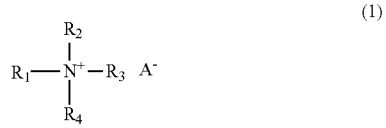

(1)

The groups $R_1$, $R_2$, $R_3$ and $R_4$ can vary within wide limits and examples of quaternary ammonium compounds that have anti-microbial properties will be well known to the person of ordinary skill in the art. Typically, two of $R_1$, $R_2$, $R_3$ and $R_4$ are lower alkyl, meaning having 1 to 4 carbon atoms, such as methyl, ethyl, propyl or butyl groups. In addition, two of $R_1$, $R_2$, $R_3$ and $R_4$ are longer chain alkyl groups of 6 to 24 carbon atoms, or a benzyl group. $A^-$ is a monovalent anion or one equivalent of a polyvalent anion of an inorganic or organic acid. Suitable anions for $A^-$ are in principle all inorganic or organic anions, in particular halides, for example chloride or bromide, carbonates, bicarbonates, carboxylates sulfonates, phosphates or a mixture thereof.

It has been discovered that a specific mixture of quat provides shorter contact kill times when used in a particular ratio and in the presence of a particular class of surfactants. This mixture of quaternary ammonium compounds includes a first quaternary ammonium compound (component (i)) which is a dimethyldialkyl ammonium compound having between 8 and 10 carbon atoms in each of the alkyl groups. The second quaternary ammonium compound (component (ii)) is an alkyl dimethyl benzyl ammonium compound, wherein the alkyl group contains between 10 and 18 carbon atoms. The alkyl group of the benzyl ammonium compound may be alky groups, such as $C_{12}$ alkyl, $C_{14}$ alkyl and $C_{16}$ alkyl. Component (ii) may also be a blend of alkyl dimethyl benzyl ammonium compounds. It has been discovered that when a mixture of compounds, as described here, is used as the quaternary ammonium compound, a reduced contact time is needed to have effective kill of the *Pseudomonas aeruginosa* (Pa), *Salmonella enterica* (Se) and *Staphylococcus aureus* (Sa).

Examples of dimethyldialkyl ammonium compounds which may be used as component (i) include dimethyl dioctyl ammonium compounds such as dimethyl dioctyl ammonium chloride, dimethyl didecyl ammonium compounds such as dimethyl didecyl ammonium chloride and the like. Mixtures of dimethyldialkyl ammonium compounds may also be used and other anions, such as those described above may also be used. Commercially available dimethyldialkyl ammonium compounds include, for example, BARDAC™ LF-80, BARDAC™ 22 which are available from Lonza America, Inc. having offices in Allendale, N.J., and the like. Other similar commercially available quats may also be used.

Examples of alkyl dimethyl benzyl ammonium compounds useable as component (ii) include $C_{12}$ alkyl dimethyl benzyl ammonium chloride, $C_{14}$ alkyl dimethyl benzyl ammonium chloride, and $C_{16}$ alkyl dimethyl benzyl ammonium chloride. In addition, a mixture of these alkyl dimethyl benzyl ammonium compounds can be used. Commercially available alkyl dimethyl benzyl ammonium compounds include, for example BARQUAT® 50-65, BARQUAT® 50-65B, which are available from Lonza America, Inc. having offices in Allendale, N.J., and the like. These commercially available alkyl dimethyl benzyl ammonium compounds are blends of $C_{12}$, $C_{14}$, and $C_{16}$ alkyl dimethyl benzyl ammonium chlorides. Generally, it is preferable that the alkyl dimethyl benzyl ammonium compound, when a blend, contains higher concentrations of $C_{12}$ alkyl and $C_{14}$ alkyl components than $C_{16}$ alkyl components. It is noted that other anions, including those mentioned above may also be used.

In the disinfectant concentrate, the weight ratio of component (i) to component (ii) is between 4:1 to 1:2. More typically, the ratio of component (i) to component (ii) is in the range of about 2:1 to about 1:1. A specific example of a weight ratio useable in the present invention is 1.5:1 component (i) to component (ii).

In the disinfectant concentrate, the disinfectant component (i) and component (ii) will make up about 40% to about 60% by weight of the disinfectant concentrate.

In addition to the disinfecting component, the disinfectant concentrate contains a surfactant. Typically, the surfactant will be a nonionic surfactant or a cationic surfactant. The surfactant is present in an amount between about 1% to about 20% by weight of the disinfectant concentrate. Typically, the surfactant will be between 2% and 15% by weight of the concentrate.

A particularly suitable nonionic surfactant is an alkoxylated alcohol surfactant. It has been discovered that selection of the surfactant is a feature of the present invention that allows the composition to achieve the 5 minute kill time. It was discovered that the choice of surfactant can act to hinder the biocidal action of the composition or to potentiate (improve) the biocidal action of the composition. Particularly suitable surfactants are alkoxylated alcohol surfactant will generally have between about 2 to about 8 moles of alkoxylation. Typically, there will be between 3 and 6 moles of alkoxylation. One particular example is about 4.5 moles of alkoxylation. In addition to having the degree of alkoxylation, the alcohol which is alkoxylate will be a $C_6$-$C_{12}$ alkyl alcohol. In one embodiment, the alkyl alcohol is a $C_8$-$C_{10}$ alkyl alcohol. The alkoxylation may be ethoxylation. Generally, it is desirable to have the HLB (hydrophilic-lipophilic balance) to be in the range of 8-14, and more generally between 10 and 12, for example about 11. A commercially available surfactant useable in the present invention is NOVEL® 810-4.5 Ethoxylate, or Alfonic® 810-4.5, both available from Sasol North America.

A particular cationic surfactant is a quaternary ammonium compound such as an alkyl trimethyl ammonium salt. The salt anion may be an inorganic or an organic anion. Exemplary anions include, halides, for example chloride or bromide, carbonates, bicarbonates, carboxylates, sulfonates, phosphates or a mixture thereof. The alkyl group contains at least 8 carbon atoms and will generally contain between 10 and 18 carbon atoms. One particular cationic surfactant is a N-coco N,N,N trimethylammonium chloride. This surfactant is commercially available as Barquat™ CT-35 which has a mixture of alkyl chain lengths in the alkyl group, generally 70% $C_{12}$, 25% $C_{14}$ and 5% $C_{16}$. Other available surfactants include Carsoquat™ CT-429 and Carsoquat™ CT-425.

Also present in the disinfectant concentrate is a solvent. Generally, the solvent will be a polar solvent such as water, or a water-miscible solvent, such as an alcohol and/or a glycol ether. Exemplary solvents include, water, ethanol, isopropyl alcohol and the like. The solvent is added in an amount such that the other components remain with in a working range, such that the concentrate, when diluted for use, will retain its 5 minute kill time under the Use Dilution Test.

Additionally, the concentrate of the present invention may contain an optional sequestering agent. Sequestering agents include, for example, acetic acid derivative selected from the group consisting of ethylenediaminetetraacetic acid (EDTA), nitrilotriacetic acid (NTA), tetrasodium EDTA. The ability of NTA and EDTA to remove metal ions facilitates of the solution by preventing hardness (calcium) precipitation. The sequestering agent may also serve to bind other metal ions that may adversely affect the effectiveness of the disinfecting components in the composition. In addition, sequestering agent may also assist in soil removal and/or preventing soil redeposition into the disinfecting composition while in use. The sequestering agents, when present in the concentrate is generally present in an amount up to about 20% by weight, and are typically present in an amount of about 2 to about 8% by weight.

The disinfectant concentrate of the present invention may also contain a pH adjusting agent. Suitable pH adjusting agents include sodium hydroxide, sodium citrate and other similar compounds. In the present invention, the concentrate and the use disinfectant composition will have a pH in the range of about 6 to about 13. Generally the disinfectant composition will be considered a neutral disinfecting composition if the pH is in the range of about 6 to about 8. The disinfectant composition will be considered an alkaline disinfectant composition when the pH is in the range of above 8 to about 12.

The disinfecting concentrate of the present invention may optionally further contain corrosion inhibitors, complexing agents, auxiliaries, preservatives, fragrances, colorants and the like. Exemplary corrosion inhibitors include, for example, organic phosphorous compounds and blend of organic phosphorous compounds with a polymeric component. Exemplary auxiliaries include, for example, polyethylene glycol or other similar compounds. Colorants and fragrances may be added provided they do not interfere with the function of the composition and may serve for identifying the composition. Generally, the optional further ingredients will make up less than about 20% by weight of the composition.

The composition of the present invention is generally provided as a concentrate, as described above. Prior to using the disinfectant concentrate, the composition must be diluted with water to prepare a disinfecting composition, which may then be used. Depending on the exact concentration of the disinfecting components in the concentrate, the concentrate will be diluted with water in a ratio somewhere between 64 parts of water and 1024 parts of water per part of the disinfectant concentrate. Generally, the dilution will be between 128 part of water and 512 parts water per part of the disinfectant concentrate. A specific example is 256 parts water per part of the disinfectant concentrate, which translates to 2 gallons of water per ounce of the disinfectant concentrate. Again, it all depends on the amount of the disinfecting component (a). Typically, the desired amount of the disinfecting component (component (i) and component (ii) in the disinfecting composition for use is in the range of about 800 ppm to about 1600 ppm. The amount of the disinfecting component in the disinfecting composition may be higher, depending on the final end use. Typically, the disinfecting component will be in the range of about 1000 ppm to about 1300 ppm in the final disinfecting composition.

The disinfecting composition of the present invention may be applied to a substrate to be treated using conventional application techniques. Conventional techniques include spraying, pouring, squirting and/or wiping the disinfecting composition on a substrate. The composition is provided to the end user as a ready-to-use disinfecting composition and is provided to the end user in a container with an application means. For example, the composition may be provided in a container which is pressurized as an aerosol, a container with a trigger or pump sprayer, as a squirt container or conventional containers with a removable cap that allows the user to pour the disinfecting composition onto a substrate.

The present invention is further described in detail by means of the following Examples. All parts and percentages are by weight and all temperatures are degrees Celsius unless explicitly stated otherwise.

EXAMPLES

Example 1

A disinfectant concentrate composition was prepared by mixing the following components listed in TABLE 1 in the specified amounts, by the method outlined below.

TABLE 1

| Component | Amount | Active amount |
| --- | --- | --- |
| Water | 90.64 g | 90.64 g |
| Sodium Citrate | 4.0 g | 4.0 g |
| Na$_4$EDTA 39% solution | 14.0 g | 5.46 g |
| Bardac ™ LF-80 | 38.4 g | 30.78 g |
| Barquat ® 50-65B | 40.96 g | 20.48 g |
| Linear ethoxylated alcohol (Novel ® 810-4.5) | 12 g | 12 g |

Components of TABLE 1 were mixed by mixing the granular sodium citrate with tap water and a 39% solution of sodium ethylenediaminetetraactic acid to form a solution. A commercially available dioctyl dimethyl ammonium chloride Bardac™ LF-80, available from Lonza America, Inc., Allendale, N.J. (an 80 wt % solution of the dioctyl dimethyl ammonium chloride in a 50-50 mixture of ethanol and water) was added to the solution and a commercially available alkyl dimethyl benzyl ammonium chloride Barquat® 50-65B, available from Lonza America, Inc., Allendale, N.J. (a 50% solution of a blend of alkyl dimethyl benzyl ammonium chlorides in water) was also added. The blend of alkyl dimethyl benzyl ammonium chlorides contains about 67% $C_{12}$ alkyl dimethyl benzyl ammonium chloride, 25% $C_{14}$ alkyl dimethyl benzyl ammonium chloride, about 7% $C_{16}$ alkyl dimethyl benzyl ammonium chloride and less than about 2% $C_{18}$ alkyl dimethyl benzyl ammonium chloride. In addition, a commercially available surfactant, NOVEL® 810-4.5 Ethoxylate, which is a $C_{8-10}$ alcohol ethoxylated with about 4.5 moles of ethoxylation, was added to the mixture. The mixture was stirred for a period of time to ensure thorough mixing of the components. The resulting composition had a pH of about 12.4. This composition formed the disinfectant concentrate.

One part of disinfectant concentrate was added to 256 part deionized water which was synthetically modified to have a 250 ppm of hardness to form a disinfecting composition.

The resulting disinfecting composition was tested for efficacy against *P. aeruginosa* and *S. aureus* using AOAC Use Dilution Test (UDT) of 2012 methodology 964.02 and 955.12, respectfully, at 5 minutes contact time, the test method incorporated by reference.

By this method, it is desirable to have less than 2 tubes showing growth at the end of the challenge. The disinfecting composition had only one positive test tube, thereby passing the UDT for a five minute contact time.

Example 2

A neutral disinfectant composition was prepared by mixing the following components listed in TABLE 2 in the specified amounts via the method outlined below.

TABLE 2

| Component | Amount | Active amount |
|---|---|---|
| Water | 19.38 g | 19.38 g |
| EDTA acid | 1.0 g | 1.0 g |
| Na$_4$EDTA 39% solution | 8 g | 3.12 g |
| Bardac ™ LF-80 | 24.98 | 19.98 g |
| Barquat ® 50-65B | 26.64 g | 13.32 g |
| Barquat ™ CT-35 | 29 g | 10.15 g |

Components of TABLE 1 were mixed by mixing the ethylenediaminetetraactic acid with tap water and a 39% solution of sodium ethylenediaminetetraactic acid to form a solution. A commercially available dioctyl dimethyl ammonium chloride Bardac™ LF-80, available from Lonza America, Inc., Allendale, N.J., (an 80 wt % solution of the dioctyl dimethyl ammonium chloride in a 50-50 mixture of ethanol and water) was added to the solution and a commercially available alkyl dimethyl benzyl ammonium chloride Barquat® 50-65B, available from Lonza America, Inc., Allendale, N.J. (a 50% solution of a blend of alkyl dimethyl benzyl ammonium chlorides in water) was also added. The blend of alkyl dimethyl benzyl ammonium chlorides contains about 67% C$_{12}$ alkyl dimethyl benzyl ammonium chloride, 25% C$_{14}$ alkyl dimethyl benzyl ammonium chloride, about 7% C$_{16}$ alkyl dimethyl benzyl ammonium chloride and less than about 2% C$_{18}$ alkyl dimethyl benzyl ammonium chloride. In addition, a commercially available cationic surfactant, Barquat™ CT35 was added to the mixture. The mixture was stirred for a period of time to ensure thorough mixing of the components. The resulting composition had a pH of about 7. This composition formed the disinfectant concentrate.

One part of disinfectant concentrate was added to 256 part deionized water which is synthetically modified to have a 250 ppm of hardness to form a disinfecting composition.

The resulting disinfecting composition was tested for efficacy against *P. aeruginosa* and *S. aureus* using AOAC Use Dilution Test (UDT) of 2012 methodology 964.02 and 955.12 at 5 minutes contact time.

By this method, it is desirable to have less than 2 tubes showing growth at the end of the challenge. The disinfecting composition had a single positive test tube, thereby passing the UDT for a five minute contact time.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A disinfectant composition having a 5 minute or less contact kill time as measured by the Use Dilution Test of 2012, said composition consisting of:
    a) a disinfecting component being a mixture of:
        (i) a dimethyldialkyl ammonium compound, and
        (ii) an alkyl dimethyl benzyl ammonium compound, wherein the components are in a weight ratio of component (i) to component (ii) between 4:1 to 1:2;
    b) a nonionic or cationic surfactant;
    c) a solvent;
    d) optionally a sequestration agent;
    e) optionally a pH adjuster;
    f) optionally a corrosion inhibitor;
    g) optionally a complexing agent;
    h) optionally an auxiliary;
    i) optionally a preservative,
    j) optionally a fragrance; and
    k) optionally a colorant.

2. The disinfectant composition according to claim 1, wherein the nonionic surfactant is an alkoxylated alcohol surfactant having 2-8 moles of alkoxylation and the cationic surfactant is an alkyl trimethyl ammonium salt.

3. The disinfectant composition according to claim 2, wherein each of the alkyl groups of the dimethyldialkyl ammonium compound contains between 8 and 10 carbon atoms and the alkyl group of the alkyl dimethyl benzyl ammonium compound contains between 12 and 18 carbon atoms.

4. The disinfectant composition according to claim 3, wherein the weight ratio of dimethyldialkyl ammonium compound to the alkyl dimethyl benzyl ammonium compound is between about 2:1 to about 1:1.

5. The disinfectant composition according to claim 4, wherein the weight ratio of dimethyldialkyl ammonium compound to the alkyl dimethyl benzyl ammonium compound is about 1.5:1.

6. The disinfectant composition according to claim 5, wherein the dimethyldiakyl ammonium compound is dimethyldioctyl ammonium chloride.

7. The disinfectant composition according to claim 2, wherein the alkyl groups of the dimethyldialkyl ammonium compound are each octyl groups.

8. The disinfectant composition according to claim 7, wherein the dimethyldialkyl ammonium compound is dimethyldioctyl ammonium chloride.

9. The disinfectant composition according to claim 2, wherein the alkoxylated alcohol surfactant has between 4-6 moles of alkoxylation.

10. The disinfectant composition according to claim 2, wherein the dimethyldiakyl ammonium compound is dimethyldioctyl ammonium chloride, the alkyl group of the alkyl dimethyl benzyl ammonium compound contains between 12 and 18 carbon atoms; the weight ratio of dimethyldialkyl ammonium compound to the alkyl dimethyl benzyl ammonium compound is about 1.5:1, wherein the alkoxylated alcohol surfactant has between 4-6 moles of alkoxylation.

11. The disinfectant composition according to claim 1, wherein the sequestration agent is EDTA, and the pH adjuster is sodium citrate.

12. The disinfecting composition according to claim 1, wherein of the disinfecting component (a) is present in a range of about 800 ppm to about 1600 ppm.

* * * * *